(12) United States Patent
Kawabe et al.

(10) Patent No.: US 6,880,409 B2
(45) Date of Patent: Apr. 19, 2005

(54) CURVED PANEL SHEAR TEST APPARATUS

(75) Inventors: Shun Kawabe, Wako (JP); Keiichi Sato, Wako (JP)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 13 days.

(21) Appl. No.: 10/679,407

(22) Filed: Oct. 7, 2003

(65) Prior Publication Data

US 2004/0069072 A1 Apr. 15, 2004

(30) Foreign Application Priority Data

Oct. 8, 2002 (JP) ........................................ 2002-295225

(51) Int. Cl.⁷ ................................................ G01N 3/02
(52) U.S. Cl. ...................................................... 73/856
(58) Field of Search .......................... 73/841, 843, 846, 73/849, 852, 853, 854, 856

(56) References Cited

U.S. PATENT DOCUMENTS

| | | | | |
|---|---|---|---|---|
| 2,256,306 A | * | 9/1941 | Ziegler | 83/445 |
| 5,140,861 A | * | 8/1992 | Gleason et al. | 73/865.8 |
| 6,253,626 B1 | * | 7/2001 | Shoberg et al. | 73/862.044 |
| 6,698,296 B1 | * | 3/2004 | Heike et al. | 73/856 |
| 6,716,097 B1 | * | 4/2004 | Freund et al. | 452/149 |

FOREIGN PATENT DOCUMENTS

JP          60-135839 A        7/1985

* cited by examiner

*Primary Examiner*—Max Noon
(74) *Attorney, Agent, or Firm*—Birch, Stewart, Kolasch & Birch, LLP

(57) ABSTRACT

A shear test apparatus for testing a shear characteristic of a curved panel is provided. The shear test apparatus includes a frame made up of first and second curved side bearing members for bearing a pair of curved sides of the curved panel and first and second flat side bearing members for bearing a pair of flat sides of the curved panel. The second curved side bearing member has an arm extending in a direction perpendicular to the face of the curved panel. The arm has an external force loading point in a position coincident with the center of shear of the curved panel, to prevent twisting of the curved panel.

1 Claim, 8 Drawing Sheets

CURVED PANEL SHEAR TEST APPARATUS

This nonprovisional application claims priority under 35 U.S.C. § 119 (a) on Patent Application No. 2002-295225 filed in JAPAN on Oct. 8, 2002, which is herein incorporated by reference.

FIELD OF THE INVENTION

This invention relates to a shear test apparatus for use on a curved panel such as a fuselage outer panel of an aircraft.

BACKGROUND OF THE INVENTION

In related art there is no disclosure relating to curved panel shear test technology, but in Japanese Patent Laid-Open Publication No. SHO-60-135839 a shear tester for a rectangular panel is disclosed.

Figure 10:
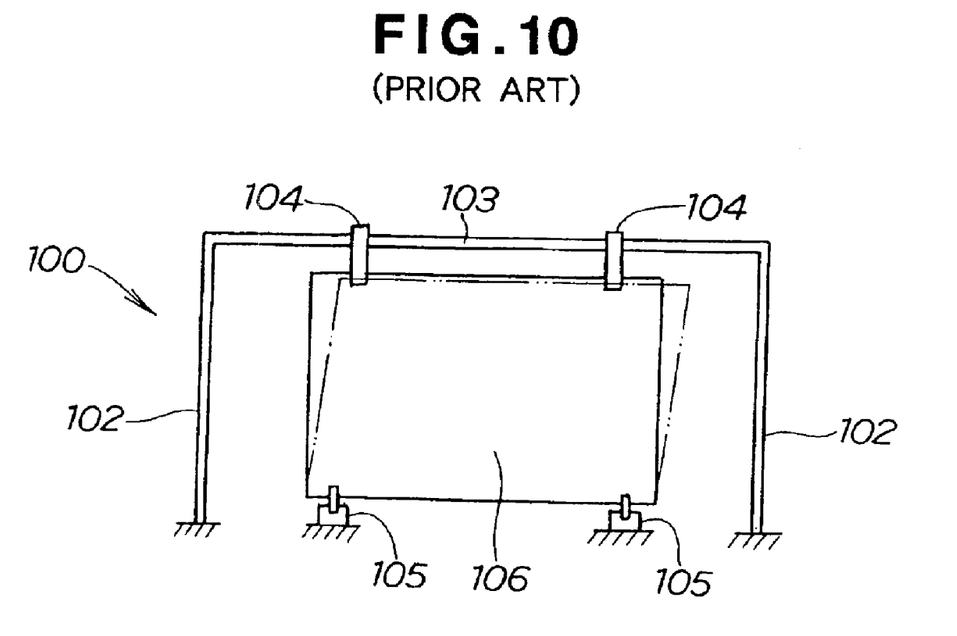
FIG. 10 is a schematic view of a rectangular panel shear test apparatus of related art.

The disclosed rectangular panel shear test apparatus is shown in FIG. 10 hereof.

The shear tester 100 shown in FIG. 10 has a rail 103 extending horizontally between a pair of posts 102, 102, supporting claws 104, 104 provided movably on this rail 103, and fixtures 105, 105 such as foundations.

One side of a rectangular panel 106 is held by the fixtures 105, 105, and the opposite side of the rectangular panel 106 is gripped by the supporting claws 104, 104. By the supporting claws 104, 104 being moved along the rail 103, a shear stress arising in the rectangular panel 106 is obtained.

The rectangular panel 106 must be a flat panel. When a shear test of a curved panel is carried out with the shear tester 100, a uniform shear load cannot be applied to the curved panel, bending of the edges of the curved panel and undulations in the center consequently arise, and an accurate shear characteristic (e.g. strength) cannot be measured.

Therefore, a shear tester of related art cannot be used on a curved panel. However, there is a need to measure accurate shear characteristics (e.g. strength) of curved panels typified by fuselage outer panels of aircraft by applying a uniform shear load to the curved panel in its curved state.

Thus, a shear tester capable of applying a uniform shear load to a curved panel has been awaited.

SUMMARY OF THE INVENTION

According to the present invention, there is provided a shear test apparatus for measuring shear characteristics of a curved panel made by curving a rectangular plate to a circular arc in cross-section and having a pair of curved sides and a pair of flat sides perpendicular to the curved sides, the apparatus including: a frame made up of a fixed first curved side bearing member and a second curved side bearing member which moves in parallel with the first curved side bearing member respectively disposed at the curved sides, and first and second flat side bearing members respectively disposed at the pair of flat sides; a plurality of pin joints provided at the four corners of the frame so as to allow the frame to deform rhomboidally; four retaining plates for holding the curved panel to the frame; a guide mechanism for suppressing movement of the second curved side bearing member in a direction perpendicular to the face of the curved panel; and an arm extending from the center of the second curved side bearing member in a direction perpendicular to the face of the curved panel and having an external force loading point at the center of shear of the curved panel, so that using the external force loading point the second curved side bearing member is forcibly moved and a shear characteristic of the curved panel is obtained from the load necessary for this movement.

The thus-arranged test apparatus prevents bending of the edge of the curved panel by holding the edge of the curved panel with the frame and retaining plates.

In an ordinary straight beam, when an external force acts parallel with the cross-section centerline at the cross-section centroid, twisting does not occur. However, in a curved beam, even if an external force acts parallel with the cross-section centerline at the cross-section centroid, twisting occurs.

A transverse centerline perpendicular to the cross-section centerline and passing through the centroid is extended to the convex side of the curved panel, and an external force at right angles to the transverse centerline is applied at a point on this transverse centerline. When the point is moved along the transverse centerline, the amount of twist changes. When the point on the transverse centerline is set at a position a certain distance away from the centroid, the twist becomes zero. The point at which the twist becomes zero like this is called the 'center of shear'.

Because the external force loading point is set at this center of shear position, the shear test can be carried out without the curved panel twisting. A uniform shear load can be applied to the curved panel, and an accurate shear characteristic (e.g. strength) can be measured.

BRIEF DESCRIPTION OF THE DRAWINGS

A presently preferred embodiment of the invention will now be described in detail, by way of example only, with reference to the accompanying drawings, in which.

DETAILED DESCRIPTION OF THE PREFERRED EMBODIMENT

Figure 1:
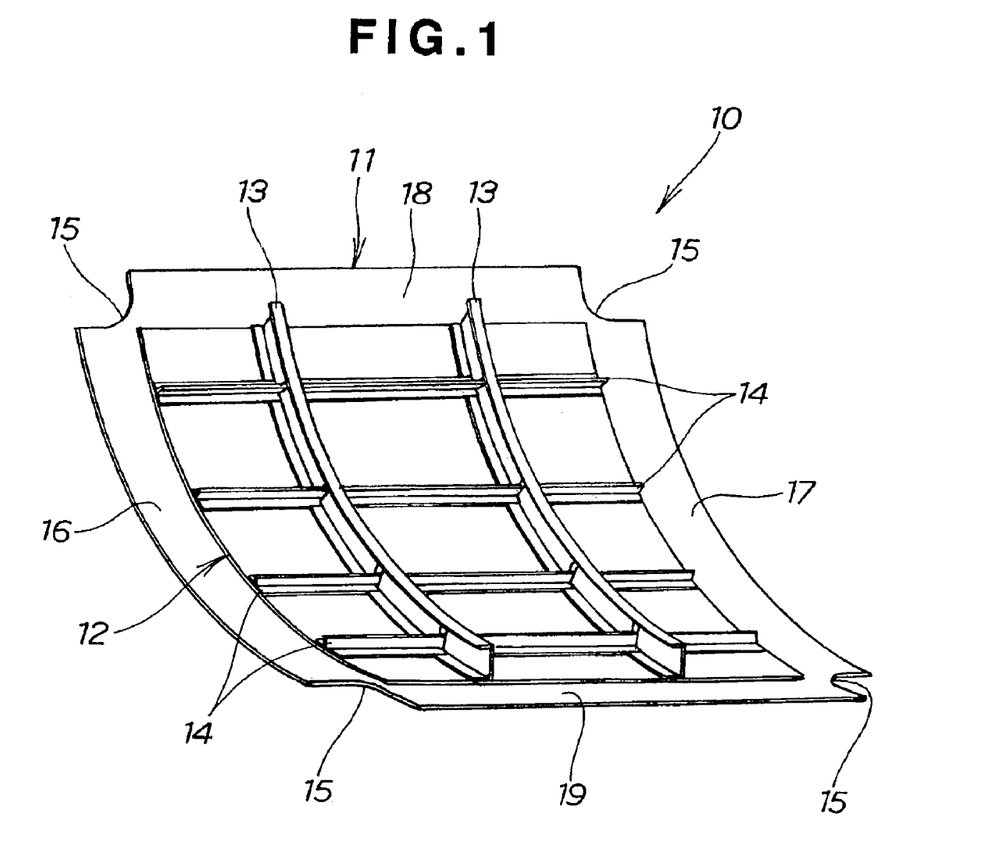
FIG. 1 is a perspective view of a curved panel used in a test apparatus of the invention.

A curved panel 10 shown in FIG. 1 for example forms part of an aircraft fuselage, and has an aluminum alloy outer skin 11, an aluminum alloy inner panel 12, multiple first reinforcing ribs 13, and multiple second reinforcing ribs 14. The first reinforcing ribs 13 and the second reinforcing ribs 14 form a grid. The outer skin 11 has cutaways 15 formed at its four corners. These cutaways 15 are provided to avoid interference with pin joints which will be further discussed later.

The four sides of the curved panel 10 comprise the pair of curved sides 16, 17 and the pair of flat sides 18, 19 perpendicular to these curved sides 16, 17.

Figure 2:
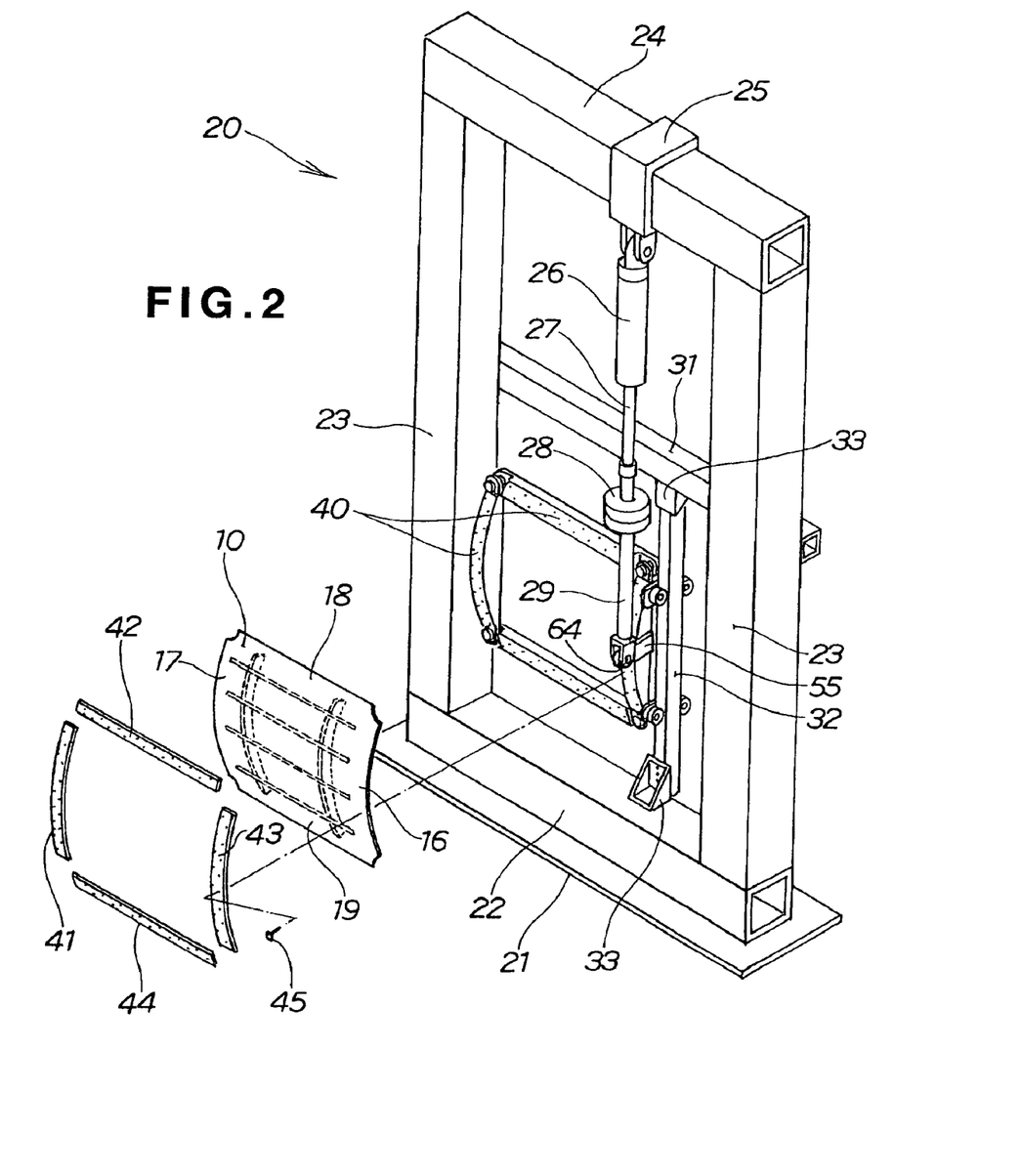
FIG. 2 is a perspective view of a curved panel shear test apparatus according to the invention.

FIG. 2 is a perspective view of a curved panel shear test apparatus according to the invention.

The curved panel shear test apparatus 20 includes a base plate 21 and a rectangular frame mounted on this base plate 21. The frame is made up of a bottom frame member 22 fixed to the base plate 21, a pair of columns 23, 23 extending vertically upward from the ends of this bottom frame member 22, and a top frame member 24 extending between the top ends of the columns 23, 23.

A surrounding band member 25 is attached around the top frame member 24, movably along the top frame member 24. A hydraulic cylinder 26 is suspended from the band-shaped member 25. A load cell 28 is attached to a piston rod 27 of this hydraulic cylinder 26. A pulling rod 29 is hung from the lower side of the load cell 28. A middle beam 31 extends between the columns 23, 23 at an intermediate height position. A guide rail 32 is provided running vertically between this middle beam 31 and the bottom frame member 22. The bottom end of this guide rail 32 is connected to the bottom frame member 22 by a bracket 33, and the top end is connected to the middle beam 31 by another bracket 33. A frame 40 is provided between the guide rail 32 and one of the columns 23. The curved panel 10 is supported by four retaining plates 41, 42, 43, 44 and multiple retaining bolts 45 accessory to this frame 40.

The load cell 28 is a device for measuring the pulling force arising in the hydraulic cylinder 26. The shear characteristics (e.g. strength) are measured by processing strain information measured by means of numerous strain gauges (not shown) affixed to the curved panel 10.

After the curved panel 10 is placed on the frame 40, bolt holes are made in the curved panel 10 in alignment with female threads formed in the frame 40. This operation is called gauging. Accordingly, in FIG. 2 the bolt holes have not yet been made in the curved panel 10.

Figure 3:
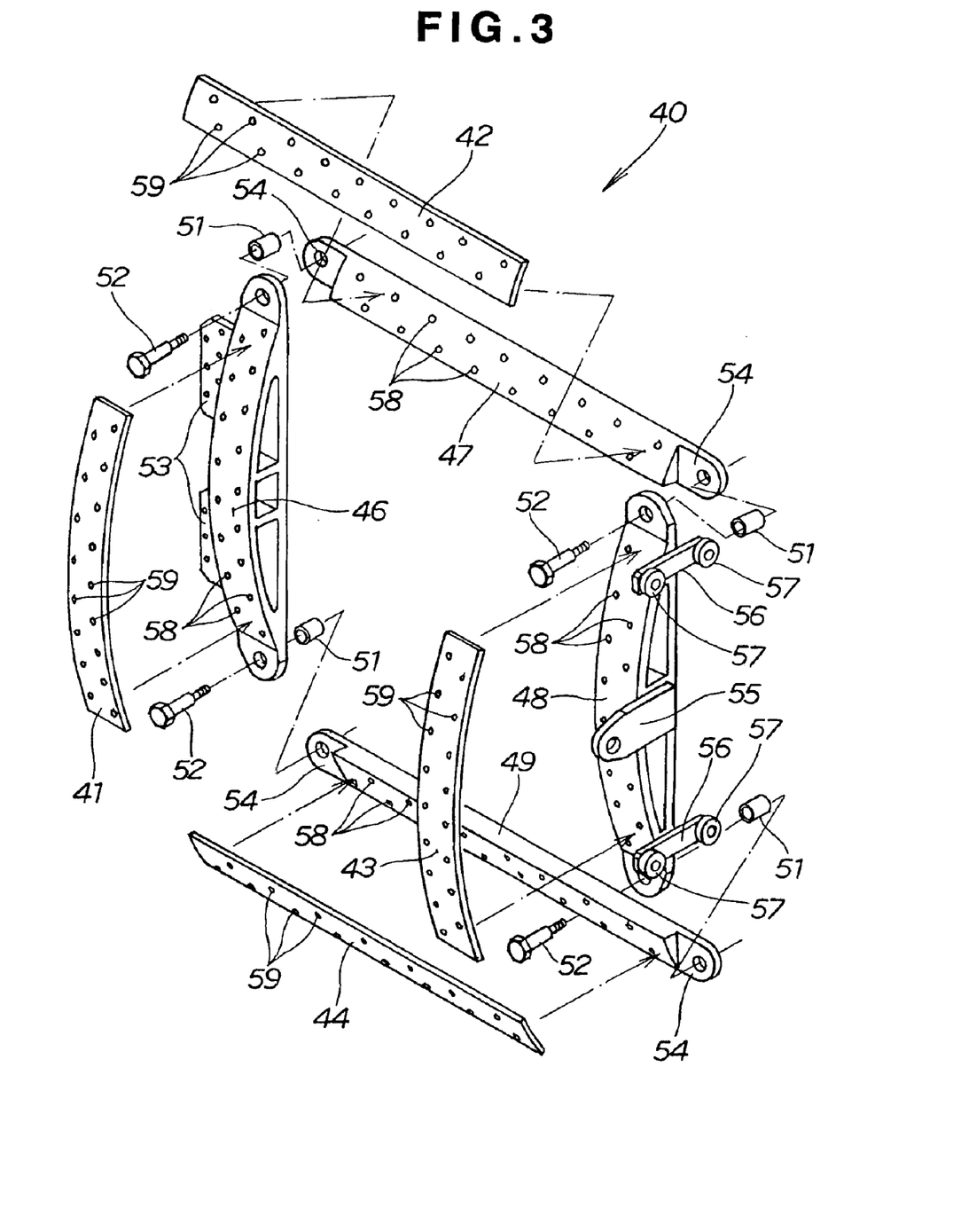
FIG. 3 is an exploded perspective view of a frame shown in FIG. 2.

The frame 40 shown in FIG. 3 is made up of a first curved side bearing member 46 facing the retaining plate 41, a first flat side bearing member 47 facing the retaining plate 42, a second curved side bearing member 48 facing the retaining plate 43, a second flat side bearing member 49 facing the retaining plate 44, and multiple collars 51 and multiple pin joint bolts 52 connecting together the bearing members 46 through 49. The first curved side bearing member 46 has fixing flanges 53, 53. The first and second flat side bearing members 47, 49 each have tongue parts 54, 54 at their ends. The second curved side bearing member 48 has an arm 55 at its center and roller support brackets 56, 56 at its ends. These roller support brackets 56, 56 have a pair each, four in total, of cam followers 57.

The first and second curved side bearing members 46, 48 and the first and second flat side bearing members 47, 49 each have numerous female threads 58 arranged in a zigzag pattern. Multiple bolts holes 59 are formed in the retaining plates 41 through 44 so as to face these female threads 58.

Figure 4:
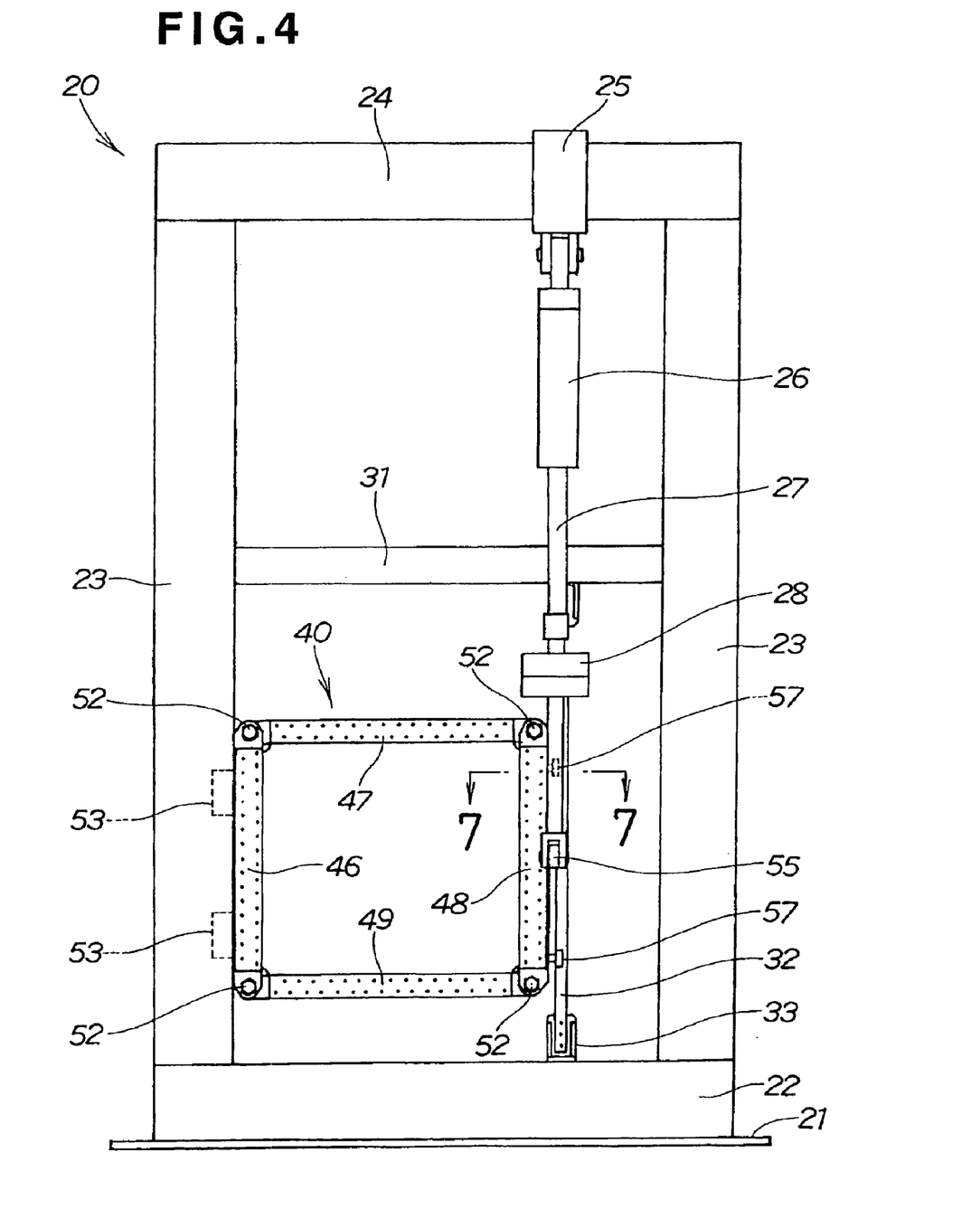
FIG. 4 is a front view of the curved panel shear test apparatus shown in FIG. 2.

As shown in FIG. 4, the fixing flanges 53, 53 are used to fix the first curved side bearing member 46 to one of the columns 23. The fixing is carried out by welding and/or with bolts.

The first and second flat side bearing members 47, 49 are connected to this first curved side bearing member 46 by two of the pin joint bolts 52, 52 and are supported in cantilever style swingably up and down about these pin joint bolts 52, 52 at the upper and lower ends of the first curved side bearing member 46. The second curved side bearing member 48 is connected to the ends of these first and second flat side bearing members 47, 49 by another two pin joint bolts 52, 52. The second curved side bearing member 48 is a moving member supported so as to be movable up and down.

Figure 5:
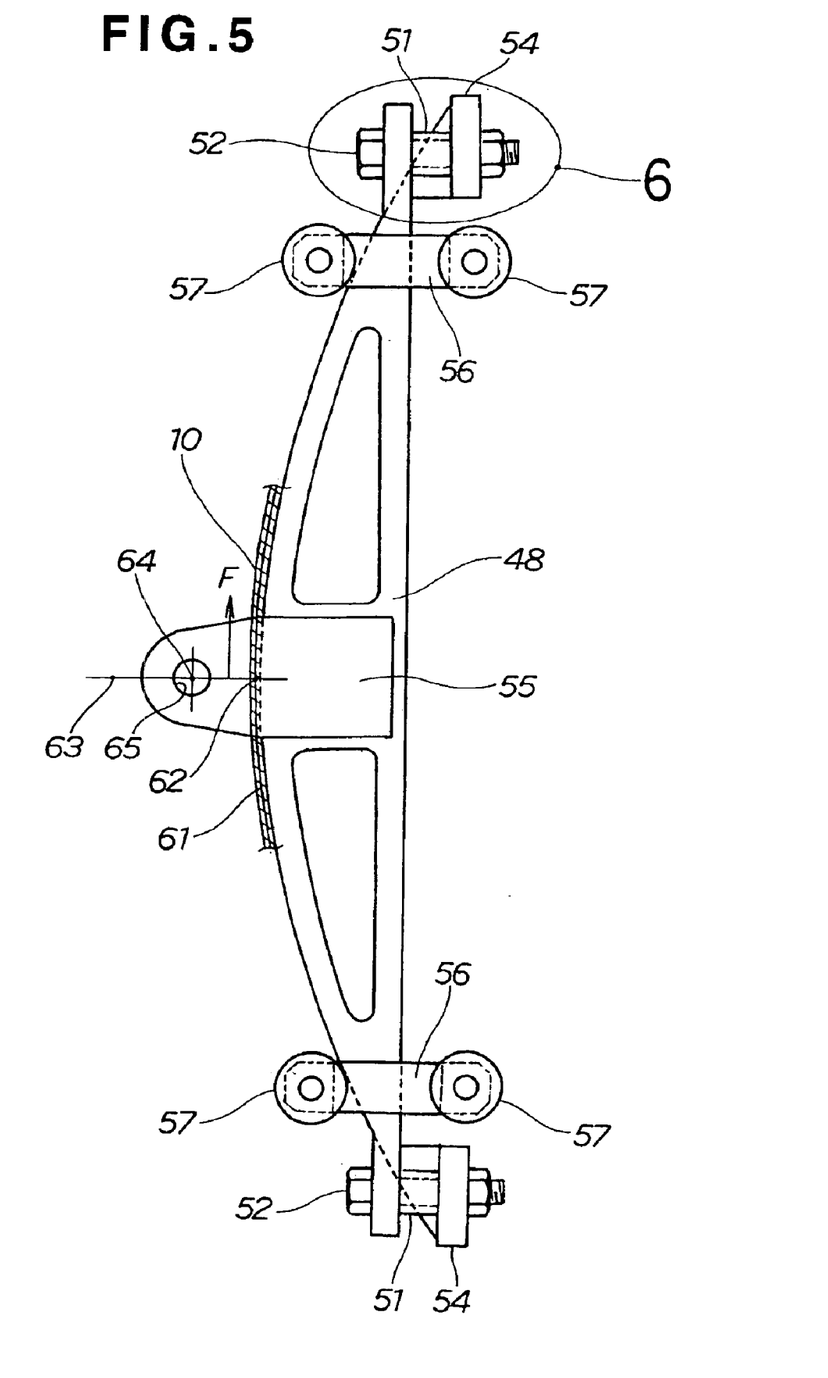
FIG. 5 is a side view of a second curved side receiving member shown in FIG. 3.

FIG. 5 is a side view of the second curved side bearing member 48.

In an ordinary straight beam, when an external force acting parallel with the cross-section centerline 61 acts at the cross-section centroid 62, twisting does not occur. However, in a curved beam (the curved panel 10), if an external force acting parallel with the cross-section centerline 61 acts at the cross-section centroid 62, twisting occurs.

A transverse centerline 63 perpendicular to the sectional centerline 61 and passing through the centroid 62 is extended to the convex side of the curved panel 10, and an external force F perpendicular to the transverse centerline 63 is applied at a point on this transverse centerline 63. When the point is moved along the transverse centerline 63, the amount of twist changes. When the point is set on the transverse centerline at a position a certain distance away from the centroid 62, the twist becomes zero. The point at which the twist becomes zero like this is called the center of shear 64.

It is a characteristic of this invention that, because the point at which the external force acts is set at the position of this center of shear 64, a pin hole 65 is provided in the arm 55 there.

That is, the arm 55 is extended from the middle of the second curved side bearing member 48 in a direction perpendicular to the face of the curved panel (the transverse centerline 63 direction), and the point of the arm 55 at which the external force is to be applied (the pin hole 65) is set in a position coincident with the center of shear 64 of the curved panel 10.

Figure 6:
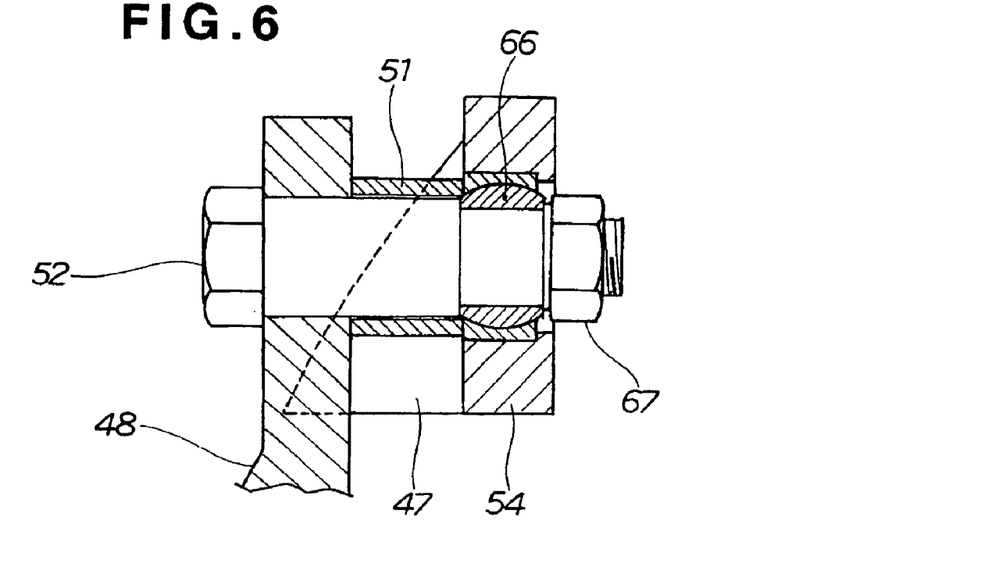
FIG. 6 is an enlarged sectional view of the detail 6 in FIG. 5.

FIG. 6 is an enlarged sectional view of the detail 6 in FIG. 5, and illustrates the construction of a pin joint in detail.

Although it has not been explained up to now, a bush 66 with a spherical surface is incorporated into each of the tongue parts 54, and the tongue parts 54 are brought together with the second curved side bearing member 48 with these spherical bushes 66 and the collars 51 therebetween, and the pin joint bolts 52 are passed through them and fastened with nuts 67.

'Pin joint' is a term of structural mechanics opposite to 'rigid joint', a joint connecting two members rigidly, and means a form of joint such that the rotation about the bolt shafts of the pin joint bolts 52 is allowed, but movement in the bolt shaft direction is not allowed. The spherical surface bushes 66 are not essential, but if the spherical surface bushes are 66 interposed, a slight amount of leaning of the pin joint bolts 52 relative to the tongue parts 54 is possible.

With this leaning allowed, lack of alignment of the curved panel with respect to the frame 40 can be absorbed, that is, high accuracy of positioning of the individual curved panel becomes unnecessary, and also damage to the pin joint bolts 52 can be prevented.

Figure 7:
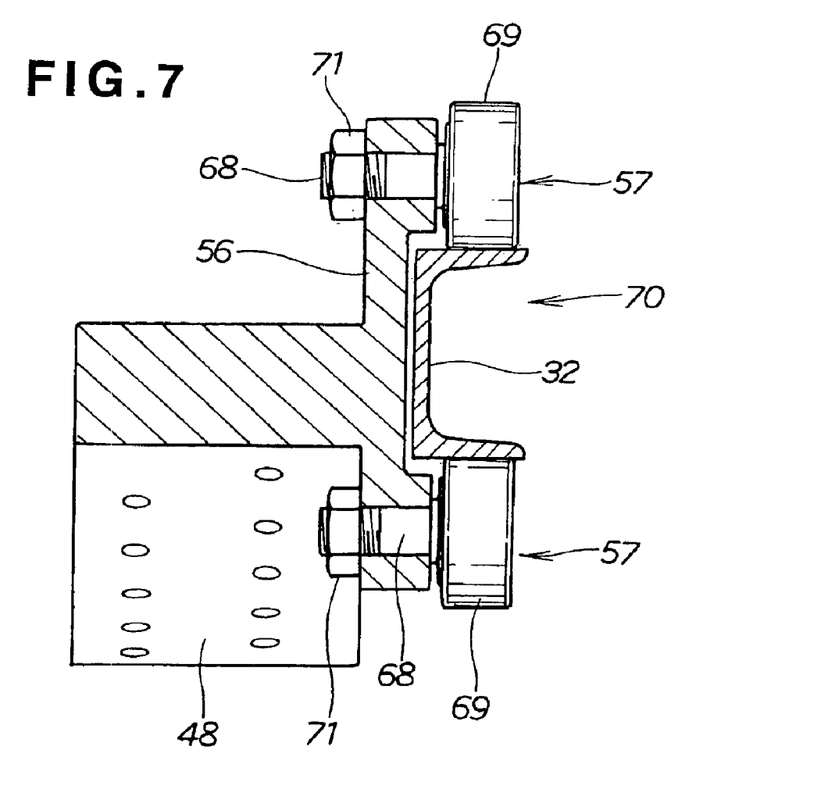
FIG. 7 is an enlarged sectional view taken along line 7—7 of FIG. 4.

FIG. 7 is a sectional view taken along line 7—7 of FIG. 4, illustrating the construction of a guide mechanism made up of cam followers and a guide rail.

The cam followers 57 are assemblies made by attaching rollers 69 to bolt shafts 68 by way of bearings, and they are mounted just by passing the bolt shafts 68 through the roller support brackets 56 and fastening them with nuts 71.

The roller support brackets 56 move in the front/rear direction of the figure with the rollers 69 on flanges of the guide rail 32, which is shaped to form a channel. That is, the guide mechanism 70 of this invention is made up of the guide rail 32 and the rollers 69 sandwiching this guide rail.

As a result of the guiding action of the guide rail 32, the roller support brackets 56 do not move in the up-down direction of the figure. However, as is clear from the figure, they can move in the left-right direction of the figure.

It is desirable for them to be movable in the left-right direction of the figure, because then in FIG. 4 they do not stop the second curved side bearing member 48 from bending slightly to the left, and the operation of the apparatus is made smooth.

The operation of a curved panel shear tester having the construction described above will now be explained.

Figure 8:
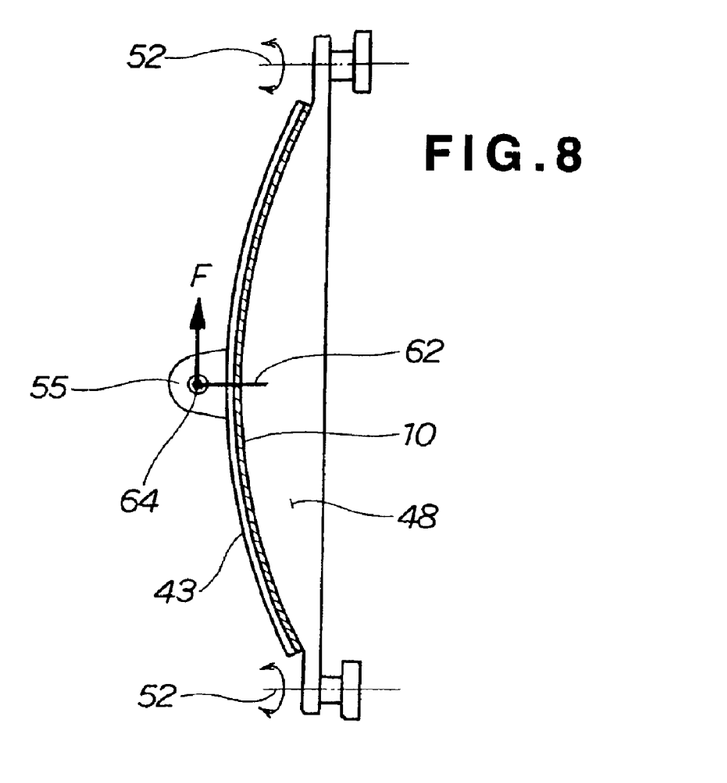
FIG. 8 is a view showing the relationship between a curved panel and a center of shear.

FIG. 8 shows the relationship between the curved panel and the center of shear in this invention. The curved panel 10 is aligned with the second curved side bearing member 48 and strongly held with the retaining plate 43. In this state, an upward external force F is applied to the center of shear 64 in the arm 55. At this time, the retaining plate 43 prevents the edge of the curved panel 10 from bending.

Figure 9:
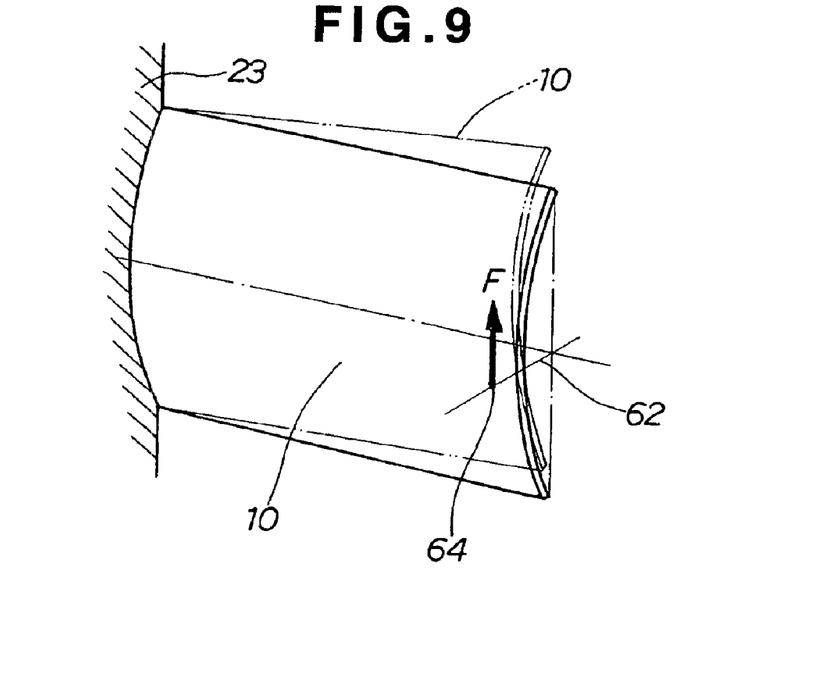
FIG. 9 is a schematic view showing movement of a curved panel during a test.

FIG. 9 shows the behavior of a curved panel during testing. Because the upward force is applied at the center of shear 64, the curved panel 10 shown with solid lines deforms slightly, without twisting, as shown with broken lines, and a uniform shear load can be applied, and as a result it is possible to measure accurately shear characteristics (e.g. strength) of the curved panel 10.

This embodiment is merely one form of the invention, and the construction of the curved panel shear test apparatus can be changed. The direction of the external force does not have to be upward, and it may alternatively be sideways or downward.

Obviously, various minor changes and modifications of the present invention are possible in the light of the above teaching. It is therefore to be understood that within the scope of the appended claims the invention may be practiced otherwise than as specifically described.

What is claimed is:

1. A shear test apparatus for measuring a shear characteristic of a curved panel made by curving a rectangular plate to a circular arc shape in cross-section so that the panel has a pair of curved sides and a pair of flat sides perpendicular to the curved sides, the apparatus comprising:

a frame including a fixed first curved side bearing member and a second curved side bearing member which moves in parallel with the first curved side bearing member, for bearing the pair of curved sides, and first and second flat side bearing members, for bearing the pair of flat sides;

a plurality of pin joints provided at the four corners of the frame so as to allow the frame to deform rhomboidally;

four retaining plates for holding the curved panel to the frame;

a guide mechanism for suppressing movement of the second curved side bearing member in a direction perpendicular to the face of the curved panel; and an arm extending from the center of the second curved side bearing member in a direction perpendicular to the face of the curved panel and having an external force loading point at the center of shear of the curved panel, so that using the external force loading point the second curved side bearing member is forcibly moved, and a shear characteristic of the curved panel is obtained from the load necessary for this movement.

* * * * *